US012551174B2

(12) United States Patent
Robar

(10) Patent No.: US 12,551,174 B2
(45) Date of Patent: Feb. 17, 2026

(54) IMMOBILIZATION DEVICES FOR RADIATION THERAPY

(71) Applicant: ADAPTIIV MEDICAL TECHNOLOGIES INC., Halifax (CA)

(72) Inventor: James L. Robar, Halifax (CA)

(73) Assignee: ADAPTIIV MEDICAL TECHNOLOGIES INC., Halifax (CA)

( * ) Notice: Subject to any disclaimer, the term of this patent is extended or adjusted under 35 U.S.C. 154(b) by 0 days.

(21) Appl. No.: 18/820,908

(22) Filed: Aug. 30, 2024

(65) Prior Publication Data

US 2025/0072847 A1 Mar. 6, 2025

Related U.S. Application Data

(60) Provisional application No. 63/536,336, filed on Sep. 1, 2023.

(51) Int. Cl.
*A61N 5/10* (2006.01)
*A61B 6/04* (2006.01)

(52) U.S. Cl.
CPC .... *A61B 6/0421* (2013.01); *A61N 2005/1097* (2013.01)

(58) Field of Classification Search
None
See application file for complete search history.

(56) References Cited

U.S. PATENT DOCUMENTS

2008/0276349 A1* 11/2008 Hsieh ........................ A42B 3/10 2/412
2018/0098589 A1* 4/2018 Diamond ............... A41D 13/05
2019/0247218 A1* 8/2019 Monat ................... A61F 5/3707
(Continued)

FOREIGN PATENT DOCUMENTS

WO 2022170432 A1 8/2022

OTHER PUBLICATIONS

Robar JL, Kammerzell B, Hulick K, et al., "Novel multi jet fusion 3D-printed patient immobilization for radiation therapy", J Appl Clin Med Phys. 2022;23:e13773.
(Continued)

*Primary Examiner* — Hoon K Song
(74) *Attorney, Agent, or Firm* — Stephen Leonard; Aird & McBurney LP

(57) ABSTRACT

Methods and devices are provided for fabricating and employing patient immobilization devices during radiation treatment procedures. Immobilization devices are provided that include a thin conformal shell configured to conform to an anatomical region of a patient that is to be exposed to radiation during a radiation treatment procedure, with a rigid lattice structure extending outwardly, in an external, beam-facing direction, from the conformal shell. The rigid lattice structure confers structural rigidity to the device, and the thin cellular regions mitigate the impact of the device on a surface dose delivered to the patient or subject. The present mechanical-metamaterial-based immobilization devices incorporate structural features that confer advantageous mechanical properties and radiation transmissive properties when compared with conventional solid or mesh-based immobilization devices used in radiation therapy.

32 Claims, 14 Drawing Sheets

(56) References Cited

U.S. PATENT DOCUMENTS

| | | | | |
|---|---|---|---|---|
| 2020/0030014 | A1* | 1/2020 | Reinauer ............ | A61B 17/8872 |
| 2022/0249866 | A1* | 8/2022 | Robar .................... | B33Y 80/00 |

OTHER PUBLICATIONS

Haefner MF, Giesel FL, Mattke M, et al. "3D-Printed masks as a new approach for immobilization in radiotherapy—a study of positioning accuracy", Oncotarget. 2018;9:6490-6498.

Laycock SD, Hulse M, Scrase CD, et al., "Towards the production of radiotherapy treatment shells on 3D printers using data derived from DICOM CT and MRI: preclinical feasibility studies", J Radiotherapy Pract. 2015;14:92-98.

* cited by examiner

IMMOBILIZATION DEVICES FOR RADIATION THERAPY

CROSS-REFERENCE TO RELATED APPLICATION

This application claims priority to U.S. Provisional Patent Application No. 63/536,336, titled "IMMOBILIZATION DEVICES FOR RADIATION THERAPY" and filed on Sep. 1, 2023, the entire contents of which is incorporated herein by reference.

BACKGROUND

The present disclosure relates to immobilization devices for stabilizing patients during radiation therapy procedures.

Radiation therapy (RT) is a major treatment modality for ~50% of all patients who have cancer. Since its inception, a range of physical patient accessories have been used for treatment delivery, including fabricated shielding blocks, treatment field-specific and manually assembled compensators, and custom-made molds, bolus or brachytherapy applicators. Many of these have required manual fabrication methods that may be time consuming in the clinic and limited with regard to control over accuracy. The field has seen a trend of these devices disappearing through digitization. For example, additive manufacturing, or 3D printing, is now used commonly to produce patient photon bolus to modulate the dose distributions of electron beams or to produce patient-specific surface brachytherapy or gynecological brachytherapy applicators. The advantages of digitizing the design and fabrication processes include increased accuracy, quality control, and in some cases, much greater efficiency in the clinic.[12]

The status quo technology for patient immobilization is the manually fabricated thermoplastic mask. Examples of 3D printing patient immobilizers, for example, cranial or head-and-neck masks, are experimental and to date, no practical solution is in widespread use in clinics. However, there exist multiple motivations to provide this technology to RT facilities. Foremost may be improving upon the current patient experience with traditional thermoplastic immobilizers. Commonly and unfortunately, the mask fabrication procedure occurs near the beginning of a patient's experience in the RT clinic. Most often the thermoplastic mask material is heated using either a hot water bath or an oven, formed by hand over the skin, and the mask is left to cool and shrink on the patient's surface. Patient's anxiety associated with the mask begins early in this process: a study (N=90) among head-and-neck patients showed that 11% of patients at CT simulation, and 24% at the time of first treatment experienced anxiety sufficient to introduce interruption of the procedure (Clover K, Oultram S, Adams C, Cross L, Findlay N, Ponman, L, Disruption to radiation therapy sessions due to anxiety among patients receiving radiation therapy to the head and neck area can be predicted using patient self-report measures, Psychooncology. 2011; 20 (12): 1334-1341. doi: https://doi.org/10. 1002/pon.1854). In a separate study (N=100), 20% and 6% of head-and-neck patients reported moderate and severe anxiety due to the mask, respectively (Nixon J L, Cartmill B, Turner J, et al. Exploring the prevalence and experience of mask anxiety for the person with head and neck cancer undergoing radiotherapy. J Med Radiat Sci. 2018; 65 (4): 282-290, doi: https://doi.org/10.1002/jmrs.308). Regarding anxiety-mitigating measures, almost a third of patients indicated improvements following customization of the mask, for example, creation holes around the eyes or mouth. Although masks may indeed be required during treatment delivery, the prospective digitization of the design would allow for the customization of mask based on patient attributes, including anticipated level of anxiety. Digital design would allow for the minimization of material involved, and (as demonstrated in this work) even the customization of mask appearance, giving the patient an active role in the process. In addition, prospective per-patient engineering design would allow for selective control over rigidity, for example, making the mask more rigid at critical points for immobilization, while relaxing the fit elsewhere to improve patient comfort. These opportunities are not afforded by today's thermoplastic immobilization.

The second motivation is the elimination of the dependence of mask quality on the manual skill of the fabricator. A poor fitting mask can result from suboptimal fabrication, and also due to changes in anatomy during the course of therapy, thus compromising patient immobilization. This uncertainty is well known in practice, and qualitative studies have indicated that a majority of health professionals cite the concern that poorly made masks may lead to poorer patient outcomes. Thus, the elimination of manual fabrication of thermoplastic masks would address a clear potential failure mode.

A third motivation relates to potential improvements in efficiency. Given the need to heat, form, and cool thermoplastic materials, the status quo approach can be time and resource intensive. The fabrication may involve more than one therapist, which increases operational cost and may also consume capital resources if the fabrication is performed in the CT suite. In contrast, optical surface imaging could provide the data necessary for immobilizer design in minutes and well in advance of the CT appointment, the device could be produced in time for the CT session, without the attendance of either the patient or therapists.

For these reasons, as well as the observation of setup accuracy comparable or superior to standard devices in humans or animals, 3D printing of immobilizers has generated significant interest in the field, and a recent review was provided by Asfia et al. (Asfia A, Novak J I, Mohammed MI, Rolfe B, Kron T. A review of 3D printed patient specific immobilisation devices in radiotherapy. Phys Imaging Radiat Oncol. 2020; 13:30-35. doi: https://doi.org/10. 1016/j.phro.2020.03.003). In reports where the fabrication method was disclosed, almost 60% used fused deposition modeling (FDM) printing, that is, extrusion of a heated polymer in successive layers to form an object. The frequent use of FDM likely arises from the fact that it is readily accessible and the low cost of the technology. However, FDM produces parts with limited reliability, and printing performance may depend on environmental factors such as humidity. Resolution is limited by the extruder nozzle diameter and achieving a smooth surface requires small layer heights, which increases already long print times. FDM typically requires manual postprocessing, and complex parts such as immobilizers will involve the printing of support structures that need to be removed manually. Besides FDM, other printing technologies explored for immobilization include material jetting, selective laser sintering, stereolithography, and binder jetting.

Multi-jet fusion (MJF) printing has not been explored widely for this application and is distinctive from other printing technologies by several promising attributes. MJF involves spatially selective fusing of a polymer powder through the application of a fusing agent followed by the application of thermal energy. MJF is reported to be ~10 times faster than FDM. A commonly used material printed by MJF is PA12, an engineering-grade plastic used in a gamut of challenging applications in industry that is mechanically strong, chemically resistant to alcohols, alkalis, ethers, esters, oils, and hot water. Germane to the production of immobilizers, it is biocompatible and offers exceptional surface finish. Finally, it is among the only methods that can add a top layer in color, which may add additional advantages in radiotherapy applications.

SUMMARY

Methods and devices are provided for fabricating and employing patient immobilization devices during radiation treatment procedures. Immobilization devices are provided that include a thin conformal shell configured to conform to an anatomical region of a patient that is to be exposed to radiation during a radiation treatment procedure, with a rigid lattice structure extending outwardly, in an external, beam-facing direction, from the conformal shell. The rigid lattice structure confers structural rigidity to the device, and the thin cellular regions mitigate the impact of the device on a surface dose delivered to the patient or subject. The present mechanical-metamaterial-based immobilization devices incorporate structural features that confer advantageous mechanical properties and radiation transmissive properties when compared with conventional solid or mesh-based immobilization devices used in radiation therapy.

Accordingly, in one aspect, there is provided an immobilization device for use in radiation therapy, the immobilization device comprising:

- a thin conformal shell configured to conform to an anatomical region of a subject; and
- a rigid lattice structure extending outwardly, in an external, beam-facing direction, from the thin conformal shell;
- the rigid lattice structure enclosing a plurality of thin cellular regions, such that each thin cellular region is laterally bounded by a portion of the rigid lattice structure, and each thin cellular region has a thickness defined by a local thickness of the thin conformal shell;
- wherein the rigid lattice structure thereby confers structural rigidity to the immobilization device, and the thin cellular regions thereby mitigate an impact of the immobilization device on a surface dose delivered to the subject.

In some example implementations of the device, the rigid lattice structure comprises a honeycomb lattice.

In some example implementations of the device, the thin conformal shell has a thickness between 0.4 and 1.0 mm.

In some example implementations of the device, the rigid lattice structure has a thickness between 0.4 and 1.0 mm.

In some example implementations of the device, the rigid lattice structure has a lateral width between 0.2 mm and 1.5 mm.

In some example implementations of the device, a radius of at least one cellular region of the plurality of cellular regions is between 2 mm and 8 mm.

In some example implementations of the device, one or more of the thin cellular regions are perforated.

In some example implementations of the device, one or more of the cellular regions is perforated with a perforation having a radius between 0.6 mm and 3 mm.

In some example implementations of the device, one or more geometrical parameters associated with the rigid lattice structure vary according to a local curvature of the thin conformal shell.

In some example implementations of the device, the conformal shell and the rigid lattice structure are formed from a thermoplastic.

In some example implementations of the device, the thermoplastic includes PA12.

In some example implementations of the device, the thermoplastic includes PLA.

In another aspect, there is provided a method of fabricating an immobilization device for use in radiation therapy, the fabrication method comprising:

- obtaining surface data characterizing an anatomical region of a subject;
- employing the surface data to generate a digital model of an immobilization device according to embodiment described above; and
- employing a three-dimensional printer to fabricate the immobilization device according to the digital model.

In some example implementations of the method, the three-dimensional printer is a multi-jet fusion (MJF) three-dimensional printer.

In some example implementations of the method, the surface data is obtained using an optical surface scanning system.

A further understanding of the functional and advantageous aspects of the disclosure can be realized by reference to the following detailed description and drawings.

BRIEF DESCRIPTION OF THE DRAWINGS

Embodiments are described with reference to the accompanying drawings. In the drawings, like reference numbers can indicate identical or functionally similar elements.

DETAILED DESCRIPTION

Figure 1:
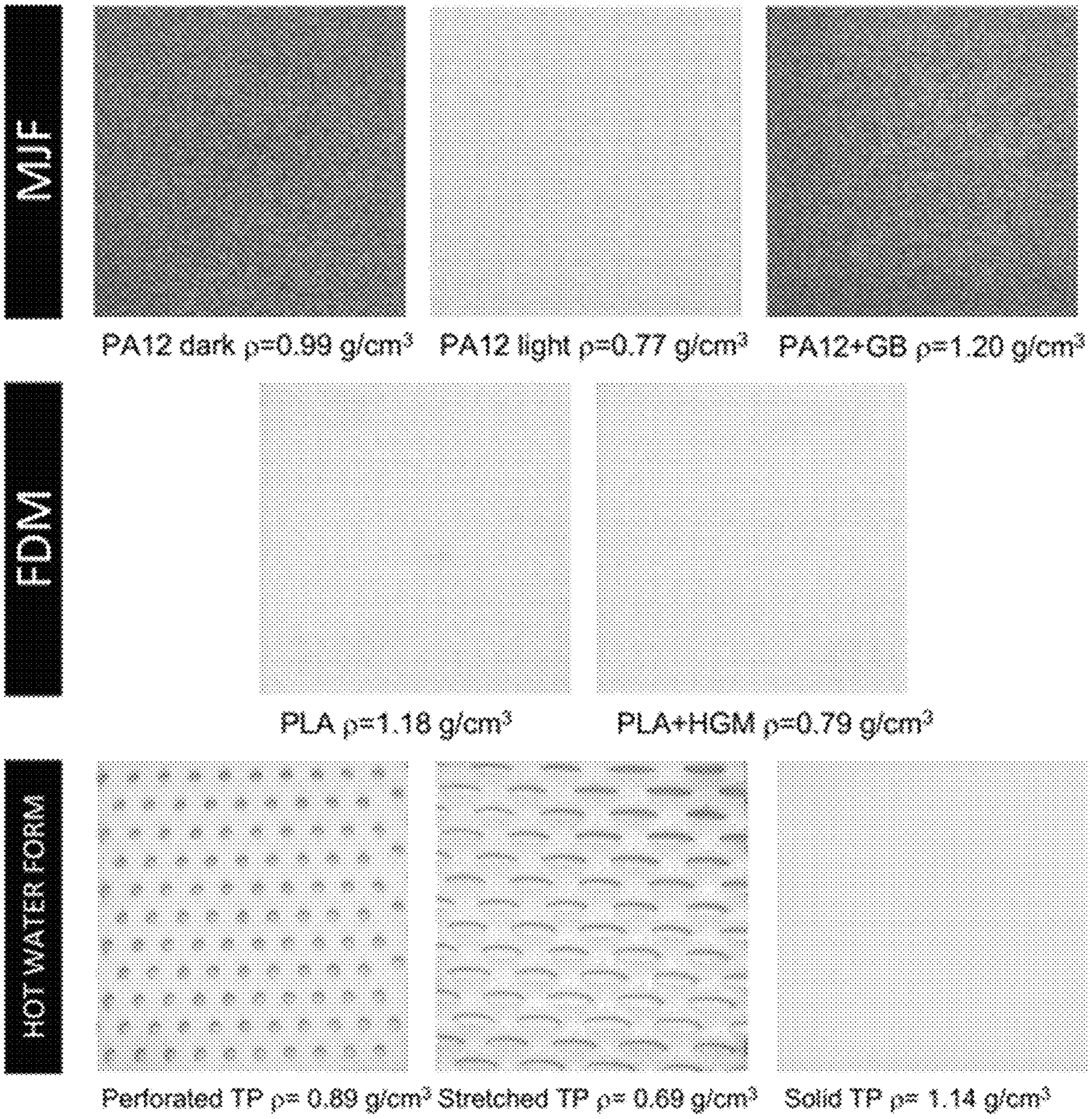
FIG. 1 shows material samples for dose build-up measurements produced by multi-jet fusion (MJF), fused deposition modeling (FDM) or by hot water-forming thermoplastic (TP). Average measured densities of samples are indicated.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. Unless otherwise specified, the terms "about" and "approximately" mean plus or minus 25 percent or less.

It is to be understood that unless otherwise specified, any specified range or group is as a shorthand way of referring to each and every member of a range or group individually, as well as each and every possible sub-range or sub-group encompassed therein and similarly with respect to any sub-ranges or sub-groups therein. Unless otherwise specified, the present disclosure relates to and explicitly incorporates each and every specific member and combination of sub-ranges or sub-groups.

As used herein, the term "on the order of", when used in conjunction with a quantity or parameter, refers to a range spanning approximately one tenth to ten times the stated quantity or parameter.

Unless defined otherwise, all technical and scientific terms used herein are intended to have the same meaning as commonly understood to one of ordinary skill in the art. Unless otherwise indicated, such as through context, as used herein, the following terms are intended to have the following meanings:

As used herein, the phrase "mechanical metamaterial" refers to a material that includes a macroscopic lattice structure or interconnected cellular structure conferring enhanced structural rigidity to the material.

The present inventor realized that the use and selection of 3D printing methods and materials introduces the opportunity of selecting or optimizing the materials in terms of radiological properties. Current thermoplastic materials have the significant disadvantage of involving significant dose buildup due to a bolusing effect of the material on the patient surface.

Among 3D printing methods, however, MJF is uncommonly versatile in that different fusing agents as well as various additives can be jetted that change material physical, optical, or electromagnetic properties. Thus, the present inventor realized that MJF 3D printing methods may facilitate the selection or development of low physical/electron density materials that reduce this bolusing effect. It was realized that the fine control on material thickness afforded by MJF printing and the ability to incorporate thin and complex features could enable a new mechanical-metamaterial-based patient immobilization device for radiation therapy that could combine the benefits of low thickness for surface dose control with the mechanical rigidity associated with the integration of an interconnected lattice.

Accordingly, various example embodiments of the present disclosure provide improved patient immobilization devices for use in radiation therapy procedures. Immobilization devices are provided that include a thin conformal shell configured to conform to an anatomical region of a patient that is to be exposed to radiation during a radiation treatment procedure, with a rigid lattice structure extending outwardly, in an external, beam-facing direction, from the conformal shell.

Figure 3:
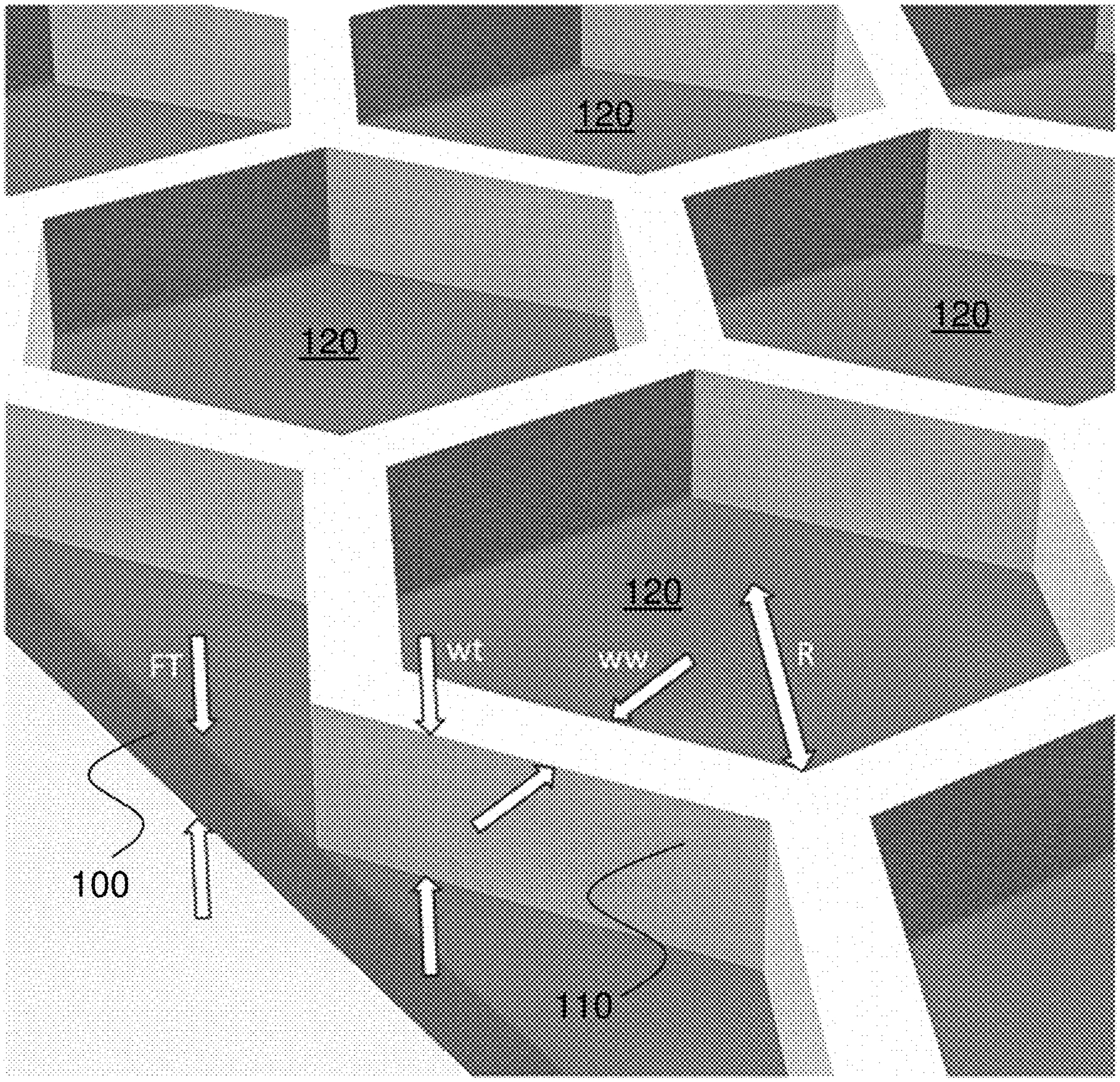
FIG. 3 shows a parameterization of a hexagonal mechanical metamaterial immobilization structure, where FT is the face thickness, ww is the wall width, wt is the wall thickness, and R is half of the inner long diagonal.

A detailed view of an example of such a structure is shown in FIG. 3. The conformal shell, shown at 100, is shaped to contour to the surface of a patient. For example, the surface of the patient can be determined according to an imaging modality including, but not limited to, structured light, LIDAR, stereographic surface imaging, and the surface-segmentation of volumetric image data obtained from imaging modalities such as computed tomography, tomosynthesis imaging, and magnetic resonance imaging. The rigid lattice structure 110 is shown extending outwardly from the conformal shell 100 in a beam-side direction. The rigid lattice structure 110 defines and encloses a set of thin cellular regions 120, such that each thin cellular region 120 is laterally bounded by a portion of the rigid lattice structure 110. As can be seen from the figure, each thin cellular region 120 has a thickness defined by a local thickness of the thin conformal shell 100.

Accordingly, an improved immobilization device is provided in which the rigid lattice structure confers structural rigidity to the immobilization device, and the thin cellular regions mitigate the impact of the device on a surface dose delivered to the patient or subject. The present mechanical-metamaterial-based design incorporates structural features that confer advantageous mechanical properties and radiation transmissive properties when compared with conventional solid or mesh-based immobilization devices used in radiation therapy.

The present invention approached the design goal of an improved immobilization device by employing a mechanical metamaterial design that yields mechanical rigidity while minimizing the amount of material required, thereby reducing the impact of the immobilization device thickness on the surface dose delivered to the patient. While a wide range of different lattice structures and geometries can be employed to form the rigid lattice structure that extends from the thin conformal shell, the example implementation shown in FIG. 3 provides an example honeycomb lattice structure that is defined (e.g. printed or formed) on the thin conformal shell.

The example honeycomb structure arises from nature: since ~36 BC, it has been speculated that bees' hexagonal structure minimizes material in filling the honeycomb while providing a highly rigid structure. Moreover, a mere 20 years ago, The Honeycomb Conjecture provided the mathematical proof that this structure minimizes total perimeter (and in the present case, material) in partitioning a plane into shapes of equal area.

In exploring the dosimetric consequences of various hexagonal geometries, a set of parameters were defined as shown in FIG. 3. Among these parameters, FT is the face thickness, that is, the thickness of the skin of material underlying or, in the case of a dual-face structure, also overlying the walls of hexagons; the width of hexagonal walls is ww and the wall thickness is wt, the total thickness is T, equal to the sum of FT and wt; and R is half the length of the inner long diagonal.

It will be understood that a wide variety of combinations of these parameters are possible. In the examples provided herein, representative values were selected that could, for some values, lead to a significant reduction in the total amount of material used and, for other values, would produce a highly mechanically robust design. For example, FT was set to either 0.4 mm to provide an extremely thin face thickness and to minimize skin dose while providing some mechanical rigidity, or alternately to 1.0 mm, which approaches the thickness of highly stretched conventional thermoplastic. The cell radius R was chosen to be 6 mm as this is small enough that it can wrap around facial features without causing design complications and is comparable to some of the perforation sizes seen in conventional thermoplastic immobilizers.

In some example implementations, the thin conformal shell may have a thickness between 0.2 and 1.5 mm, or between 0.3 and 1.2 mm, or between 0.4 and 1.2 mm, or between 0.4 and 1.1 mm, or between 0.4 and 1.0 mm, or between 0.4 and 0.9 mm, or between 0.4 and 0.8 mm. In some example implementations, the cell radius may be between 2 and 8 mm, or between 3 and 6 mm. In some example implementations, the rigid lattice structure may have a thickness between 0.2 and 1.5 mm, or between 0.3 and 1.2 mm, or between 0.4 and 1.2 mm, or between 0.4 and 1.1 mm, or between 0.4 and 1.0 mm, or between 0.4 and 0.9 mm, or between 0.4 and 0.8 mm. In some example implementations, the rigid lattice structure may have a lateral width (wall thickness) between 0.2 and 1.5 mm, or between 0.3 and 1.2 mm, or between 0.4 and 1.2 mm, or between 0.4 and 1.1 mm, or between 0.4 and 1.0 mm, or between 0.4 and 0.9 mm, or between 0.4 and 0.8 mm.

In some example implementations, one or more of the cellular regions may be perforated. In some example implementations, the radius of the perforations lie between 0.6 and 3 mm, or between 0.6 and 2 mm, or between 1 and 3 mm.

It will be understood that a wide range of topologies may be employed to define the lattice and/or local cellular structure. For example, lattices may be formed via polygonal shapes, such as pentagons or diamonds. In other examples, the rigid lattice may include an array of cell-defining structures, such as cylinders that are mutually contacting one another or connected via one or more intermediate connecting members. In some example embodiments, the lattice may define two or more differently shaped cellular regions. In some example embodiments, the rigid lattice structure may define a periodic or aperiodic (irregular) array of cellular regions. In other example embodiments, the rigid lattice structure may be configured such that the shape or geometry of the cellular regions varies among different regions of the immobilization device. In some example embodiments, one or more spatial measures associated with the rigid lattice structure may vary among different regions of the immobilization device, for example, the lattice pitch, cellular region radius, and/or perforation radius may be dependent on the local curvature of the thin conformal shell, and/or underlying anatomical features of the subject, such as bony prominences.

While the example immobilization devices disclosed herein each employ a rigid lattice structure extending outwardly from a beam-facing side of the thin conformal shell, some other example implementations may also include a second rigid lattice structure extending inwardly from a patient-facing side of the thin conformal shell. Moreover, while the example immobilization devices disclosed herein each employ a rigid lattice structure extending outwardly from a beam-facing side of the thin conformal shell, some other example implementations may include a second shell, such that the rigid lattice structure is confined between two thin shells.

Given the complex geometry of the mechanical metamaterial, one can anticipate spatial variability in the surface dose measured, that is, a higher build-up dose below the hexagonal walls with total thickness T relative to regions below smaller thickness FT. The dependence of surface dose on such parameters is explored in the Examples provided below. In general, it will be understood that a suitable set of dimensions for the rigid lattice structure and underlying thin conformal shell will vary based on clinical application, material properties, and manufacturing method employed to fabricate the structure.

In the case of the present example honeycomb structure, the present inventor has found that, relative to stretched thermoplastic used currently in the clinic, dose reductions ranging from 11% to 40% can be realized, largely depending on the face thickness of the hexagonal structure. Moreover, the dosimetric measurements and mechanical metamaterial samples employed to form this estimate were not perforated, as it may be desired to print some regions of immobilizers without perforation, and "worst case" comparisons relative to standard perforated thermoplastic were of interest. It can be expected, therefore, that perforation would lower the average build-up dose further.

Many of the examples below demonstrate how the multi-jet-fusion (MJF) process is well suited to the fabrication of various implementations of mechanical-metamaterial-based immobilization devices disclosed herein. MJF allows exceptionally fine fabrication, with printed voxels as small as 80 μm. This capability introduces opportunities for highly detailed implementations of such mechanical metamaterial designs that could be used for printing the shells of immobilizers, offering desirable mechanical and radiological properties. It will be understood that a wide range of materials may be employed to 3D print an immobilization device of the present disclosure via MJF, and that PA12 is but one example of many suitable materials.

Although MJF has been disclosed as being a suitable 3D printing method to fabricate many of the immobilization devices disclosed herein, it will be understood that other 3D printing methods, such as fused deposition modelling (FDM), and other 3D printing methods known now and in the future, may be employed to fabricate such structures. It will be understood that a suitable choice of material and fabrication method may depend on the clinical application and treatment plan.

While many of the present examples relate to cranial radiation procedures, it will be understood that the embodiments disclosed herein may be adapted to immobilize a wide range of anatomical regions for a wide range of radiation therapy procedures and modalities.

EXAMPLES

The following examples are presented to enable those skilled in the art to understand and to practice embodiments of the present disclosure. They should not be considered as a limitation on the scope of the disclosure, but merely as being illustrative and representative thereof.

The following examples consider various MJF printed materials from the point of view of the surface dosimetry of patient immobilizers. Three PA12 materials are considered, spanning a wide range of density, from 0.77 to 1.20 g/cm$^3$. Build-up dose measurements demonstrated the superiority of the PA12 material with a light fusing agent, which, at the thickness of unstretched thermoplastic, produced a lower dose even with a nonperforated sample. This material was also superior to FDM-printed samples, even after lowering the density of PLA using HGM. Example fabricated immobilizers based on the mechanical metamaterial design employing a hexagonal geometry are described, it is shown that that relative to typical stretched thermoplastic samples, dose reductions of up to 40% may be achieved. Novel MJF-printed immobilizers are demonstrated, with adult and pediatric cranial examples, as well as extended masks for head-and-neck immobilization. The MJF-printed immobilizers demonstrated excellent dimensional accuracy, with over 97% of sampled points within +2 mm.

Example 1: Methods

MJF Media Candidates and Comparison to Common Materials

In this example, three different media that are printable using MJF are considered, as well as two FDM-printable materials, with comparison to three commercially available thermoplastic immobilization samples. All printed samples were in the form of slabs ~5×5 cm$^2$ in area and were produced in thicknesses ranging from 1 to 3 mm.

FIG. 1 shows samples of each material type. The three MJF materials were printed by the manufacturer (HP) and were all based on PA12. The first is PA12 produced with the standard fusing agent and is dark in color (commercially available as "HP 3D HR PA12" printed on the MJF 5200 printer). The second is fabricated using PA12 powder with an added component, solid glass beads, and the standard fusing agent (commercially available as "HP 3D HR PA12 GB" printed on the MJF 5200 printer). The third uses a transparent fusing agent and PA12 powder with added $TiO_2$ particles. This is the standard powder used on the MJF 580 printer ("HP 3D HR CB PA12") with a custom modification to the printing mode that is not yet commercially available in which the transparent fusing agent is applied throughout the part instead of solely on the surface. These MJF materials are henceforth labeled "PA12 dark," "PA12+GB," and "PA12 light," respectively. In consultation with the manufacturer, these three materials were chosen as they span a broad range of physical density (FIG. 1) that allowed for the measurement of the dependence of surface dose on this parameter. Measured densities were 0.77, 0.99, and 1.20 g/cm$^3$ for PA12 light, PA12 dark, and PA12+GB samples, respectively. Tensile, elongation, and impact mechanical properties for PA12 MJF materials have been quantified by the manufacturer and thus are not investigated in this example.

Figure 2:
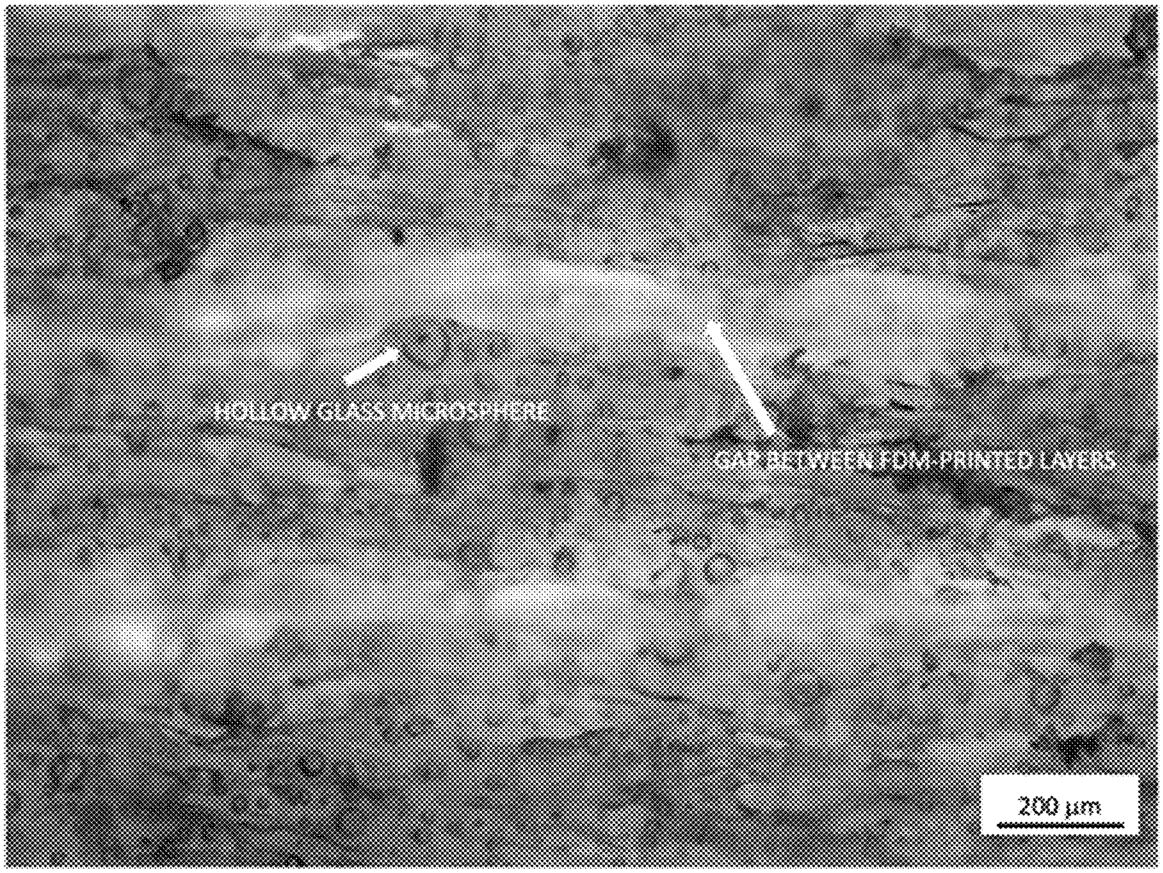
FIG. 2 shows a microscopy image showing a polylactic acid+hollow glass microspheres (PLA+HGM) material in a plane perpendicular to printed layers, illustrating the presence of intact HGM, as well as gap between layers added during the fused deposition process.

Although MJF is a promising technology to print immobilizers for the reasons stated earlier, FDM printing with polylactic acid (PLA) is among the most common methods used in RT clinics today for, for example, bolus fabrication or surface brachytherapy applicators. Thus, the MJF candidates were compared to PLA printed at 100% infill using a typical FDM printer (Taz 5, LulzBot). FDM slabs were printed using an extruder temperature of 220 C, bed temperature of 60 C, print speed of 15 mm/s, 0.5-mm layer height, and 100% infill. In addition, with a view to identifying and comparing to FDM low density materials of interest for immobilization, a second FDM material was examined, produced by extruding the same PLA material in combination with hollow glass microspheres (HGM) to reduce the density of the filament. The same printer settings were used for this PLA+HGM material as for PLA alone. The HGMs were $K_2O$ glass bubbles (3 M) with a mean particle diameter of 60 μm and an average density of 0.20 g/cm$^3$ according to manufacturer's specifications. Filament extrusion was done by mixing 30% HGMs by volume with pulverized PLA and extruding using an EX2 filament extruder (Filabot) into an FDM-printable filament of diameter 2.9 mm. Microscopy imaging (FIG. 2) confirmed the presence of intact HGMs following extrusion and also revealed the variability in a HGM diameter with many being smaller than the nominal 60 μm, as well as the presence of gaps between deposited layers that can be expected as a result of the FDM process (FIG. 2). Measurements showed that after printing, the average density among PLA+HGM samples was 0.79±0.05 g/cm$^3$ compared to the density of the standard FDM slab of 1.18 g/cm$^3$. It was found that extrusion with HGMs above 30% by volume produced filament that did not print reliably; thus; this was the lowest density material that could be produced for FDM.

Finally, for comparison to common thermoplastics used for patient immobilization today, samples of solid thermoplastic, perforated thermoplastic; and stretched thermoplastic samples (CIVCO) were included. The solid and perforated samples were 3.2 mm in thickness, whereas the stretched sample reduced the thickness to 2.4 mm and increased the perforation area by a factor of ~3-4. This stretched thickness was based on multiple samples taken from example patient immobilizers.

Dose Measurement for Material Samples

In order to measure dose below varying build-up thicknesses of materials, an advanced Markus chamber (PTW Freiburg GmbH) embedded in a 10 cm-thick solid water phantom was used, with the protective cap removed. This located the reference point at the inner surface of the 0.03-mm polyethylene entrance window, flush with the phantom surface. Measurements were made with −300-V bias and charge collected with a Standard Imaging electrometer in integrated charge mode. Given its predominance in photon treatment of cranial and head-and-neck indications, a 6-MV beam was used for all measurements, produced by a Varian TrueBeam (Varian Medical Systems) linear accelerator. A jaw-defined 4×4-cm$^2$ field size was used to examine the dosimetry under narrow field conditions. This was also chosen for practical reasons, that is, to be smaller than the 5×5-cm$^2$ slab dimensions. For all measurements, the source-to-detector distance was 100 cm. Material layers were added in increments allowing high depth-resolution (as fine as ~1.0 mm for MJF samples) to establish ionization-versus-thickness curves for the 3D printed samples extending beyond a total thickness of 15 mm. As only relative measurements among samples were of interest in this work, ionization was not converted to absolute dose through calibration factors. To plot relative dose as a function of total build-up thickness, actual slab thicknesses were measured precisely (to within 0.01 mm) using a micrometer, taking five measurements over the sample area and averaging. Given their fixed thicknesses, thermoplastic samples involved just a single layer per material type.

Mechanical Metamaterial Design for Immobilizers

Figure 4:
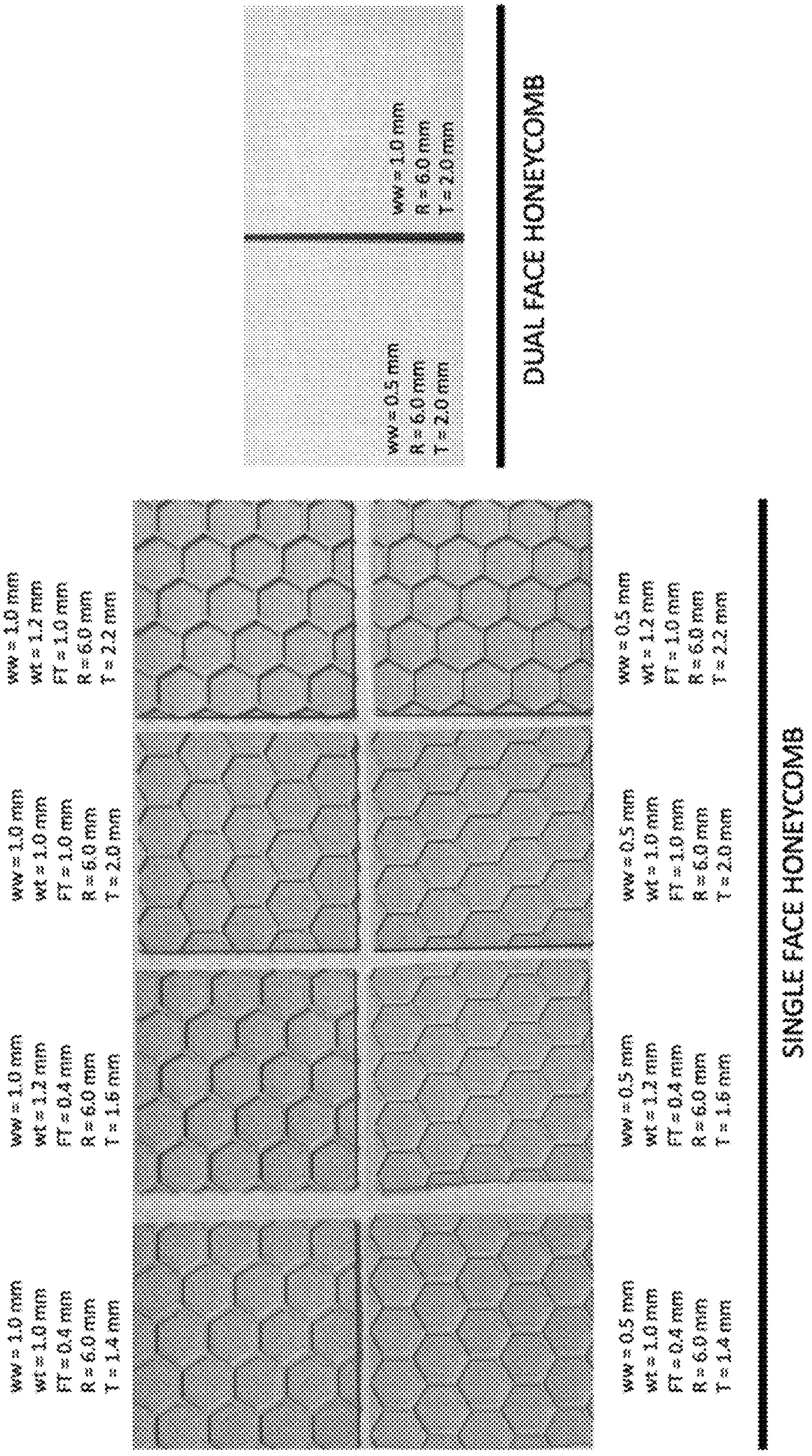
FIG. 4 shows 10 example mechanical metamaterial designs examined in the present examples, varying values of face thickness (FT), wall thickness (wt), wall width (ww). Cell radius (R) was fixed at 6.0 mm.

FIG. 4 shows images of all 10 mechanical metamaterial samples produced, where each sample was 5×5 cm$^2$ in area. The majority of these designs included a single-face rather than a dual-face design, that is, one with skins sandwiching the hexagonal structure. Although a dual-face design would likely provide more rigidity, it was anticipated that this approach might trap MJF polymer powder between faces during fabrication, thus increasing the overall radiological path length, and compromising low-dose build-up characteristics. In addition, from a patient-focused/clinical point of view, the present inventors foresee a future need to design perforated mechanical metamaterials, which may be incompatible with the dual-face design.

Dose Measurements for Mechanical Metamaterial Samples

Given the complex geometry of the mechanical metamaterial, one can anticipate spatial variability in the surface dose measured, that is, a higher build-up dose below the hexagonal walls with total thickness T relative to regions below smaller thickness FT. To measure this variation and to quantify the average build-up dose between samples, a radiochromic film dosimeter type EBT3 (Ashland) was employed, which provides a dynamic range of 0.2-10 Gy. For each exposure, a mechanical metamaterial slab was placed directly on top of the radiochromic medium, which in turn was positioned on the surface of a 10 cm-thick solid water phantom. Each exposure was conducted with 200 MU and a 6×6-cm$^2$ field. Films were digitized using an Epson 10000XL transparency scanner maintaining consistency in film orientation on the scanner bed. Calibration was performed according to the manufacturer, that is, exposing a range of film strips to known doses. All three RGB channels were used for calibration, and self-consistency between these channels was verified. The calibration comprised a dose range between 20 and 300 cGy. It was verified that measured dose values under both the FT and T thicknesses, for all samples, were in the calibrated range. In all cases, calibration and films for mechanical metamaterial samples were taken from the same film batch and were scanned and analyzed in the same session, waiting 24 h between exposure and readout.

Design and Fabrication of Cranial and Head-and-Neck Immobilizers

To design realistic prototype cranial and head-and-neck immobilizers, the male atom anthropomorphic phantom (CIRS) positioned on an S-frame immobilizer baseplate (CIVCO) and Silverman B head rest was CT imaged. The CT slice thickness was 2.5 mm. Based on these image data, the surface was defined using thresholding (HU >−800), and solid model design software (Blender) was used to create immobilizer geometries. An algorithmic software workflow was used to re-mesh the surface data, tile the hexagonal mechanical metamaterial to conform to the phantom geometry, add mouth and eye holes, and integrate features that connect to the S-frame immobilizer base plate. Many of these processes involved manual manipulation during development but can be automated in software as the design stabilizes. Multiple versions of immobilizers were created, including two different mechanical metamaterials with FT of 0.4 and 1.0 mm, wt of 1.0 mm, and ww of 1.0 mm. In addition, both cranial and head-and-neck versions were designed, for demonstration purposes. To assess the accuracy of the MJF-printed immobilizers, three-dimensional surface was acquired data using HP 3D Scan (HP). This imaging system includes a projector that casts structured light on the scanned object, two cameras for acquisition, and a rotation stage to capture views of the imaged object through 360. The system provides 0.05-mm spatial sampling with up to 2.3×10$^6$ vertices per scan. The system software allows direct comparison between the design file and the scanned surfaces, providing a frequency histogram of three-dimensional spatial deviation.

Example 2: Results

Dose Measurement for Material Samples

Figure 5:
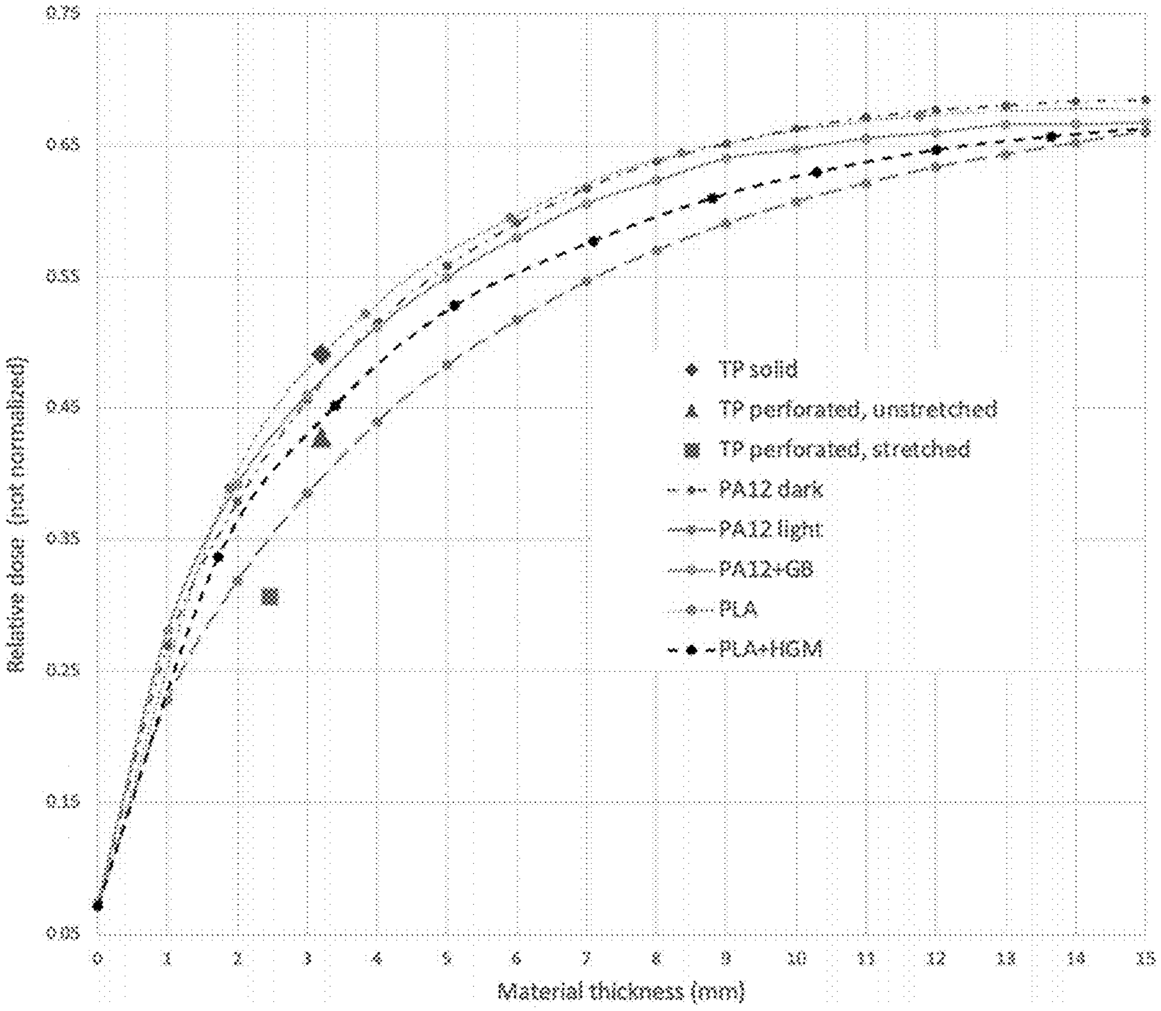
FIG. 5 plots the relative dose measured as a function of material thickness for multi-jet fusion (MJF) PA12 samples, FDM polylactic acid (PLA) samples, and single layers of solid, perforated, and perforated/stretched thermoplastic (TP).
Figure 6:
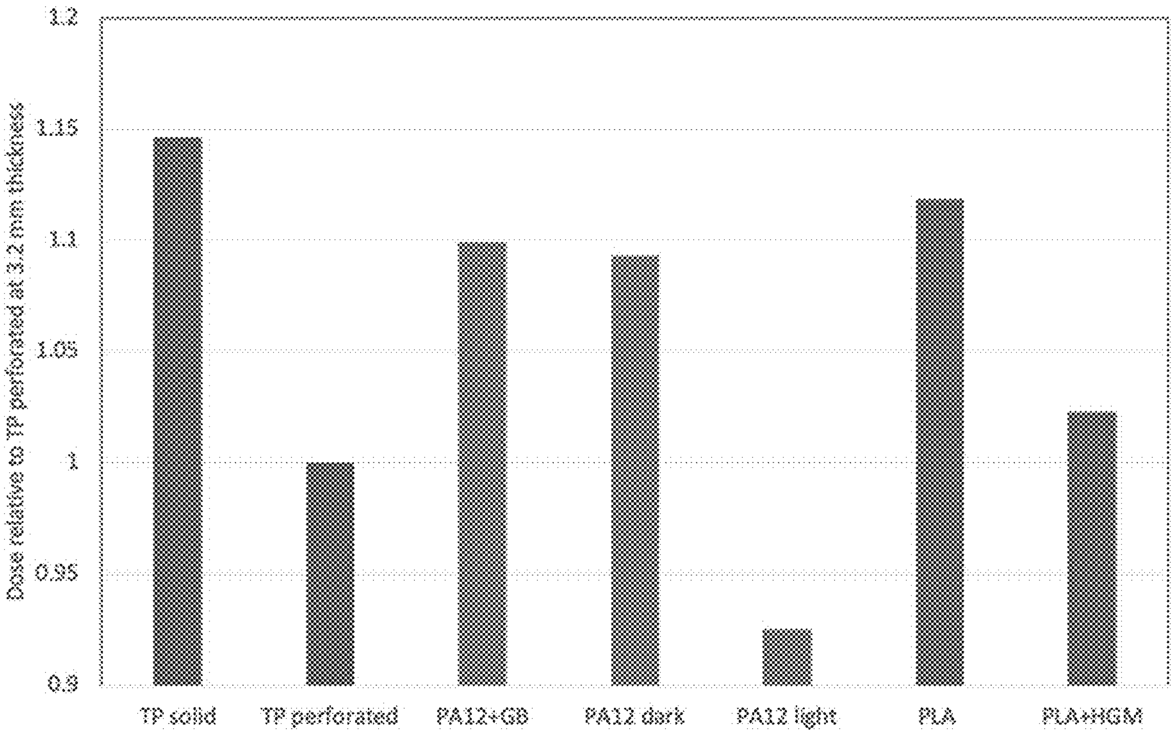
FIG. 6 plots the dose relative to perforated (unstretched) thermoplastic, for samples at a thicknesses of 3.2 mm, that is, the thickness of stock thermoplastic materials.

FIG. 5 shows measured relative dose as a function of added thickness of various sample materials, where measurements were not normalized, allowing a comparison of absolute values. At thickness values comparable to conventional masks, for example, 3 mm or less, PA12 dark, PA12+GB and standard FDM-printed PLA involve dose values within 5% of each other. The presence of HGM in PLA causes a significant reduction of dose, whereas the MJF-printed PA12 light provides the lowest value among all solid samples tested. Conventional solid thermoplastic yields dose comparable to that for PLA at the same thickness. Interestingly, although perforated, thermoplastic dose remains higher than that for a solid sample of PA12 light of the same thickness. Stretching the thermoplastic from 3.2 to 2.4 mm produces a sample with ~12% lower dose than a solid sample of PA12 light at the same thickness. The PA12 light material is also superior to the low-density FDM-printed sample containing HGMs. FIG. 6 provides a summary of measured relative dose values at a common thickness of 3.2 mm, corresponding to the stock thickness of perforated and solid thermoplastics. PA12 light appears to be a promising material for application to immobilizers, that is, even without perforations it provides a lower surface dose.

Dose Measurement for Mechanical Metamaterial Samples

Figure 7:
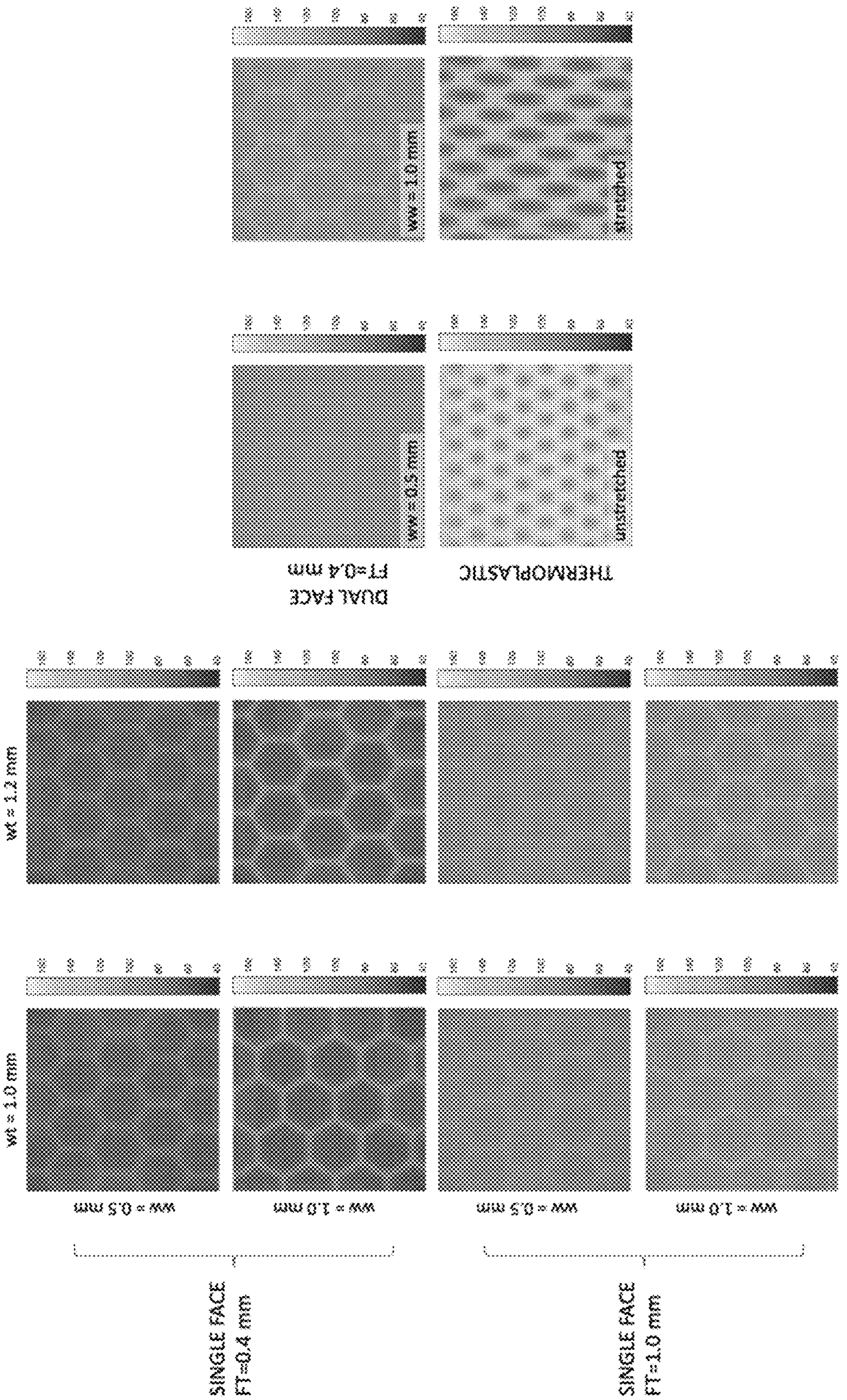
FIG. 7 shows, on left, images from radiochromic dosimetry under single-face mechanical metamaterial samples, and shows, on right, dose images for dual-face mechanical metamaterial samples as well as unstretched and stretched perforated thermoplastic. Color bars show calibrated dose in cGy.

FIG. 7 shows images resulting from radiochromic dosimetry of the mechanical metamaterial samples after calibration to dose. Shown on the left are the various samples with a single-face design, for various combinations of FT, wt, and ww. All images are shown with the same dose color scale for comparison. This demonstrates the effect of various mechanical metamaterial design parameters on dose, with single-face geometries providing much lower dose compared to dual-face designs shown on the right. Upon investigation, it was confirmed that the dual-face designs indeed trapped PA12 powder between face layers, which increases dose buildup significantly. All examples of mechanical metamaterial samples provide lower dose than either unstretched or stretched thermoplastic samples.

Figure 8:
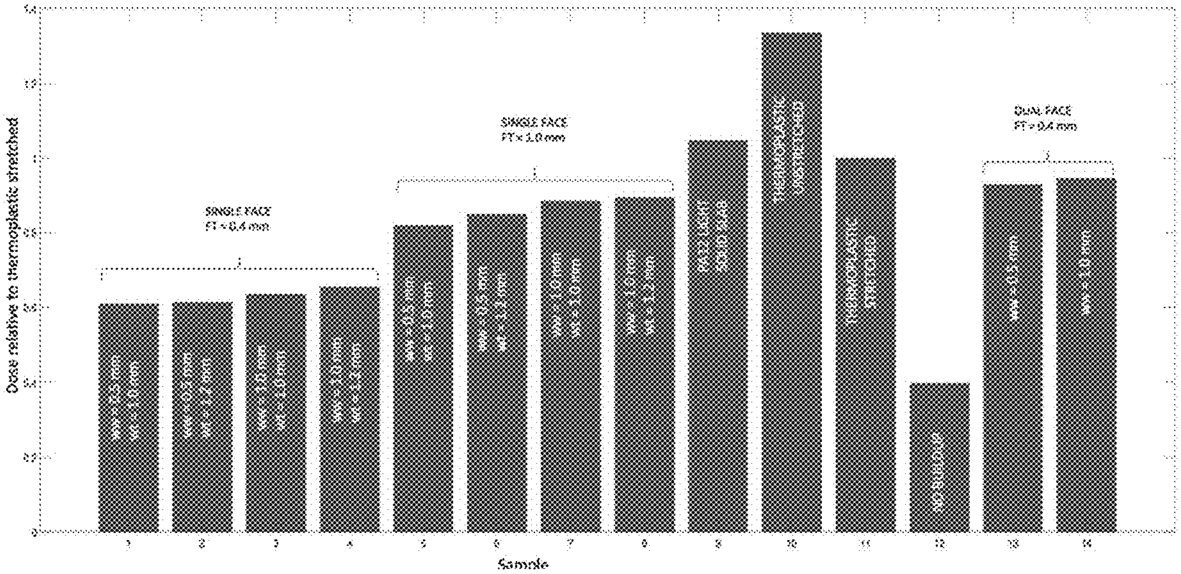
FIG. 8 plots the measured dose relative to perforated/stretched thermoplastic for all mechanical metamaterial samples.
Figure 9:
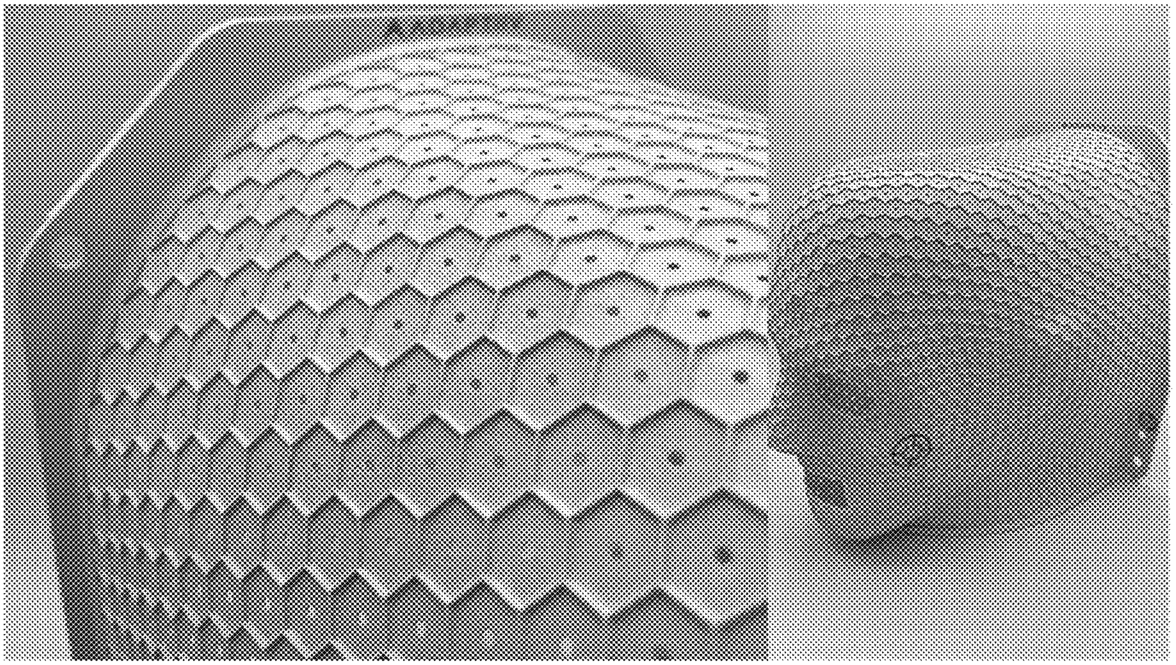
FIG. 9 shows, on the left, a multi-jet fusion (MJF)-printed immobilizer showing close-up of the mechanical metamaterial design with added perforations, and shows, on the right, the design includes a crosshair as an example of the utility of color printing in this application. This immobilizer was produced with R of 6 mm, although this value is variable with stretching around surface curvature. FT, ww, and wt were 0.4, 1.0, and 1.0 mm, respectively. Perforations had a radius of 1 mm.

Calculating average dose over the area of each sample provides the results shown in FIG. 8. Here, for practical comparison, all dose values have been normalized to that of the status quo, that is, stretched thermoplastic. In summary, dual-face mechanical metamaterial designs provide a dose reduction by as much as 7% compared to stretched thermoplastic. Single-face designs are far superior, providing significant dose reductions: by 11% to 18% for FT of 1.0, and by 35% to 40% for FT of 0.4 mm. The effect of varying wt and ww is modest, increasing these parameters produces an increase of dose by 5% to 7% for a fixed value of FT.

Design and Fabrication of Cranial and Head-and-Neck Immobilizers

Figure 10:
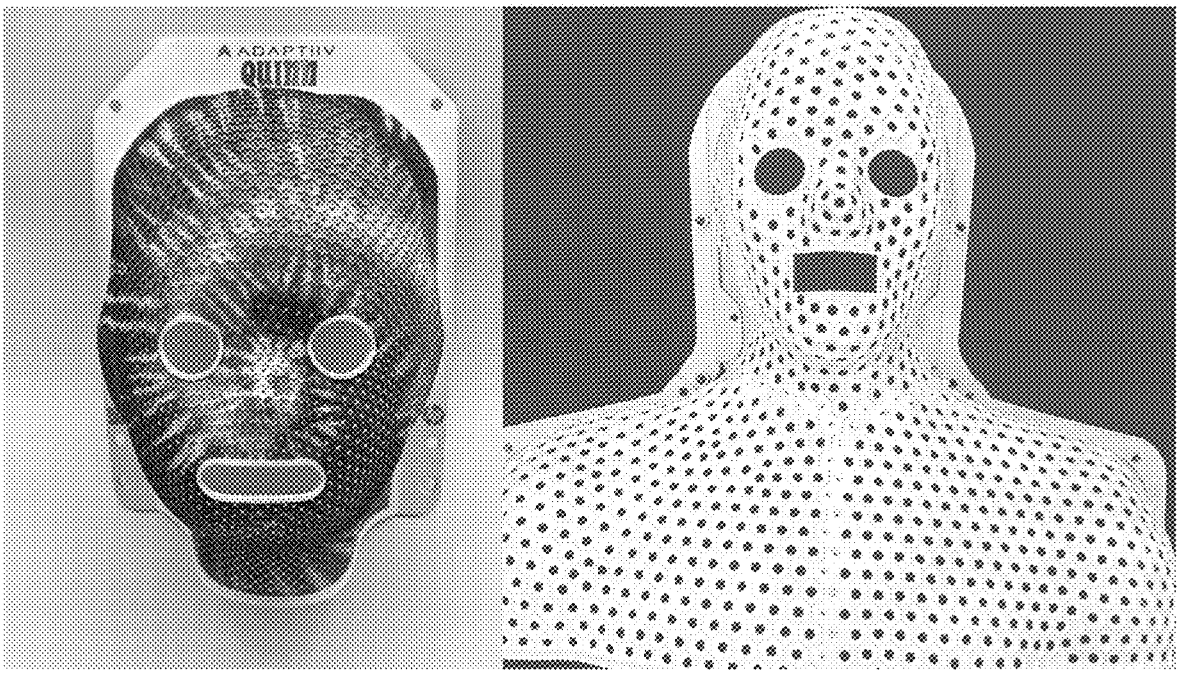
FIG. 10 shows, on the left, an example of a pediatric cranial immobilizer using the mechanical metamaterial design and printed pattern on the surface, and shows, on the right, a full head-and-neck immobilizer incorporated into a frame that is compatible with an S-type immobilizer base plate. The pediatric immobilizer was produced with an R of 3 mm, although this value is variable with stretching around surface curvature. FT, ww, and wt were 0.4, 0.5, and 0.6 mm, respectively, and perforations were 2 mm in radius. The head-and-neck immobilizer was designed with an R of 6.0 mm, with FT, ww, and wt of 1.0 mm, with 3.0-mm radius perforations.

FIG. 3 shows an example of a cranial immobilizer produced using MJF printing with a PA12 light material. Here, the prototype incorporates the mechanical metamaterial design as described earlier and illustrates the option of adding perforations centered on each hexagonal cell. FIG. 10 shows additional examples, including a pediatric cranial immobilizer, where the option of color printing has been used in a custom design. Also shown is an extended head-and-neck immobilizer. In this example, the patient-specific immobilizer has been integrated into a 3D-printed frame that is compatible with the anchor points of an S-frame type base plate.

Figure 11:
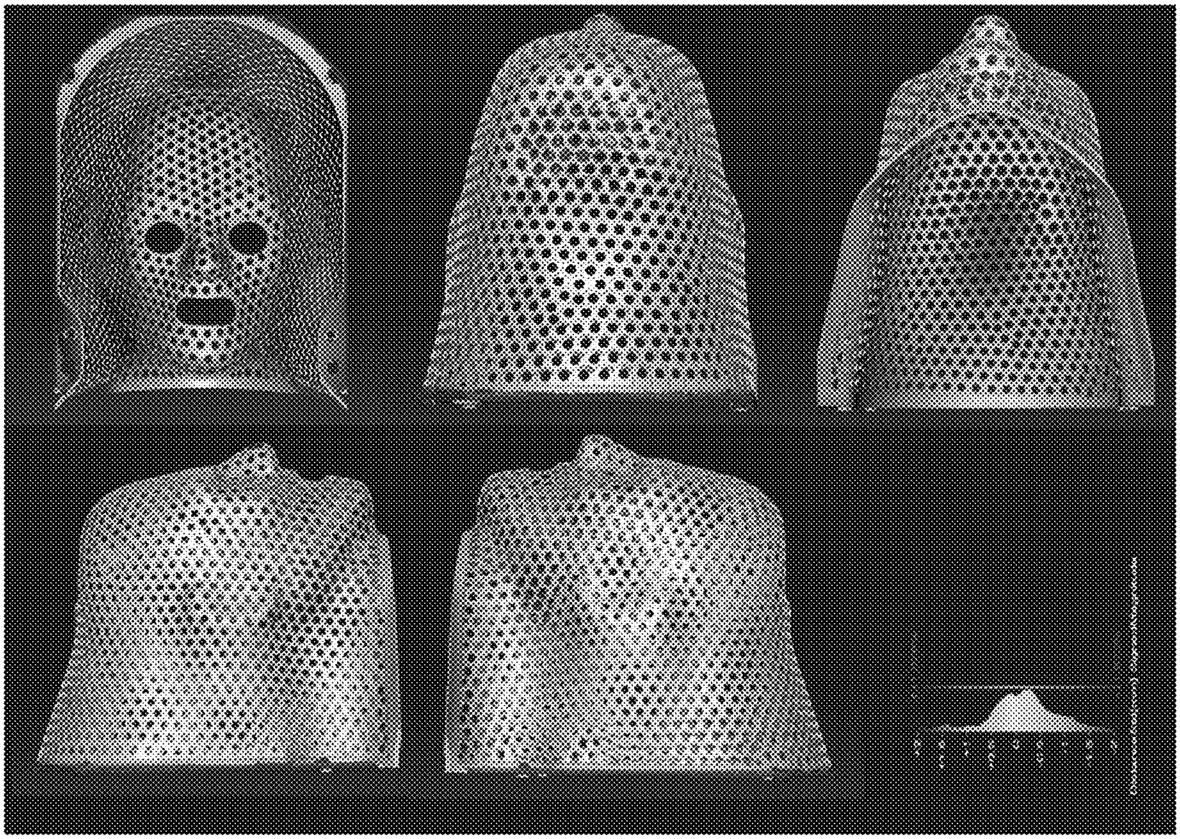
FIG. 11 presents optical scan data of adult cranial immobilizer. This immobilizer was designed with an R of 6.0 mm, with FT, ww, and wt of 1.0 mm, and with 3.0-mm radius perforations.
Figure 12:
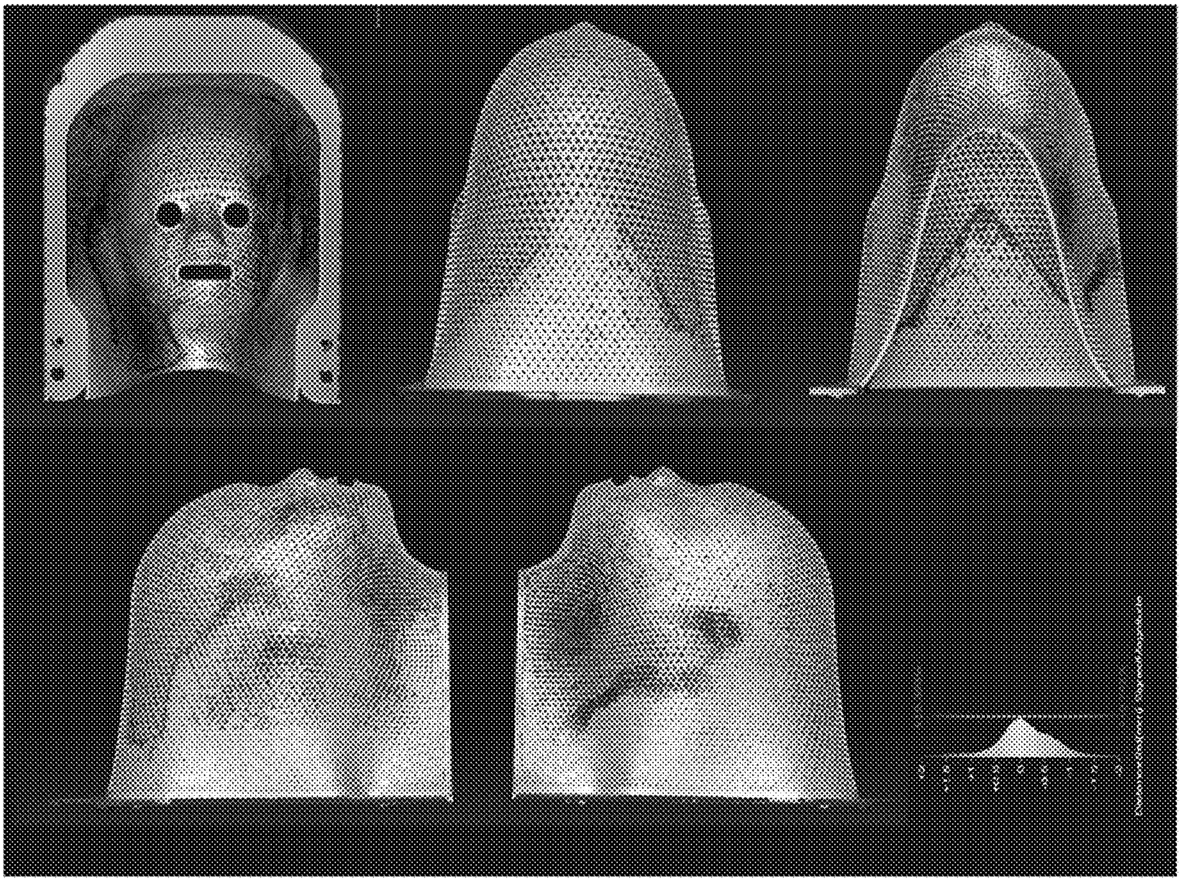
FIG. 12 shows optical scan data of a pediatric cranial immobilizer. This pediatric immobilizer was produced with an R of 3 mm. FT, ww, and wt were 0.4, 0.5, and 0.6 mm, respectively. Perforations were 0.75 mm in radius.

FIGS. 11 and 12 show example printed adult and pediatric immobilizers. An assessment of the dimensional accuracy was performed by comparing the optical scan surface to that in the design file. For the adult immobilizer, 83.4%, 97.1%, and 98.9% of sampled points show dimensional accuracy within ±1, ±2, and ±3 mm, respectively. For the pediatric immobilizer, the corresponding values are 92.5%, 98.9%, and 99.7%. It is noted that these values are based on a best fit between the designed and optically scanned surfaces and exclude the frame, which is a generic component.

Example 3: Discussion

This example has explored the potential of MJF 3D printing for the fabrication of patient immobilizers, with a focus on the impact of various MJF materials and mechanical metamaterial design on dose buildup. Aside from the benefits of digitizing/automating the design and fabrication, a material and design that lowers surface dose would be advantageous for multiple treated sites. In head-and-neck radiotherapy, grade 1-4 skin toxicity is experienced by patients, and although the causes may be multifactorial, the unwanted bolus effect of the immobilizer is consistently cited as a cause of increased skin dose. In addition, immobilization is used in treatment of multiple extracranial sites, including intact breast, where erythema and desquamation are common toxicities and conventional thermoplastic materials may increase skin dose by over 50%.

The results identify the PA12 light material as preferable with regard to dosimetry as it will provide a ~15% surface dose reduction compared to the other solid MJF materials examined. In fact, the measured dose for this material was lower than that resulting from conventional perforated thermoplastic of the same thickness. When combined with the hexagonal mechanical metamaterial design shown here, relative to stretched thermoplastic used currently in the clinic, dose reductions ranging from 11% to 40% should be realized, largely depending on the face thickness of the hexagonal structure. For these dosimetric measurements, mechanical metamaterial samples were not perforated, as it may be desired to print some regions of immobilizers without perforation, and "worst case" comparisons relative to standard perforated thermoplastic were of interest. It can be expected, however, that perforation would lower the average build-up dose further.

A study by Asfia et al. (Asfia A, Deepak B, Novak J I, Rolfe B, Kron T. Multi-jet fusion for additive manufacturing of radiotherapy immobilization devices: effects of color, thickness, and orientation on surface dose and tensile strength. J Appl Clin Med Phys. 2022; 23 (4): e13548. doi: https://doi.org/10.1002/acm2.13548) examined the possible influence of printed color and printing orientation on surface dose but did not examine different MJF materials. At 6 MV, a common photon energy for both cranial and head-and-neck treatments, no dependence of dosimetry was found on five possible colors. Tensile strength was found to depend on print orientation, for example, by ~15% for a 2-mm sample, with the 45 print orientation preferable.

The study did not measure mechanical properties of the PA12 samples as this has been reported on in depth with comparison to other 3D printing methods and already quantified in terms of tensile, elongation, and impact properties. MJF-printed PA12 has a tensile strength of 50 MPa that is higher than that of many plastics, including ABS, polyethylene, polypropylene, and polystyrene. It was observed that the immobilizers produced in this example to be robust and resilient to repeated applications to an anthropomorphic phantom. As immobilizer designs are refined, it may be beneficial to assess the mechanical robustness of devices as a whole, for example, to identify potential failure modes that may be due to the design rather than the inherent mechanical properties of the mechanical metamaterial. In addition, although the dimensional accuracy of immobilizers was found to be excellent with over 97% of sampled points within +2 mm, assessing the degree of fit to human subjects may be important, as well as the ultimate performance of the immobilizers with respect to positioning accuracy.

Aside from questions on immobilizer material, design, and fabrication, several process issues may be considered to support improved clinical workflow. If CT data are to be used as the input to immobilizer design, the fit may be dependent on the HU threshold used for surface definition, and further investigation would be beneficial to refine this value. However, in general, the use of CT may be limiting from a workflow perspective. For example, 3D surface data can be employed to design the device, yet a final treatment planning CT will typically be required with the patient positioned in the immobilizer. The option of repeating CT imaging would be suboptimal due to cost and inconvenience. However, optical surface imaging is fast, does not involve ionizing radiation, and provides excellent spatial fidelity. One can envisage acquiring these data at the time of first consultation in the clinic with the patient positioned on the immobilization baseplate and headrest, for example. Next, a practical software design application may be beneficial to offer a programmatic, efficient, and robust workflow, that is, the surface data may be employed to drive the design without the need for extensive design skills by the user. At this point, customization (eye, mouth holes, color patterns, and labeling) could be applicable. Finally, regarding timing of production and receipt by the facility, the immobilizers in this study were produced within 1 day. Thus, this may allow for a 2-day turnaround between design/order of the device and receipt, allowing the immobilizer to be available in time for a CT simulation appointment. With these provisions, the various advantages of 3D printed immobilization, including consistent quality, accuracy of fit, flexibility of design, and automation of processes, may be realized in the clinic.

Figure 13:
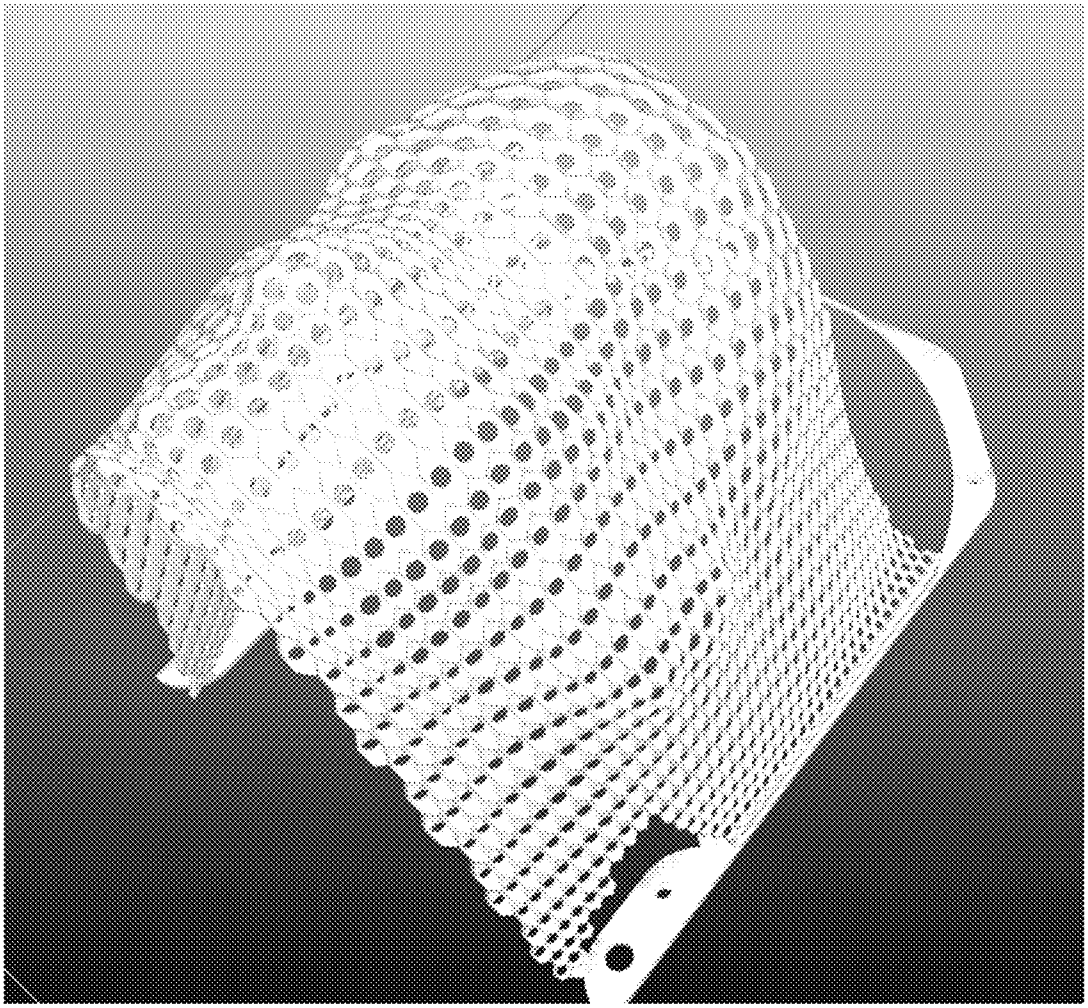
FIG. 13 shows an example fabricated immobilization device.
Figure 14:
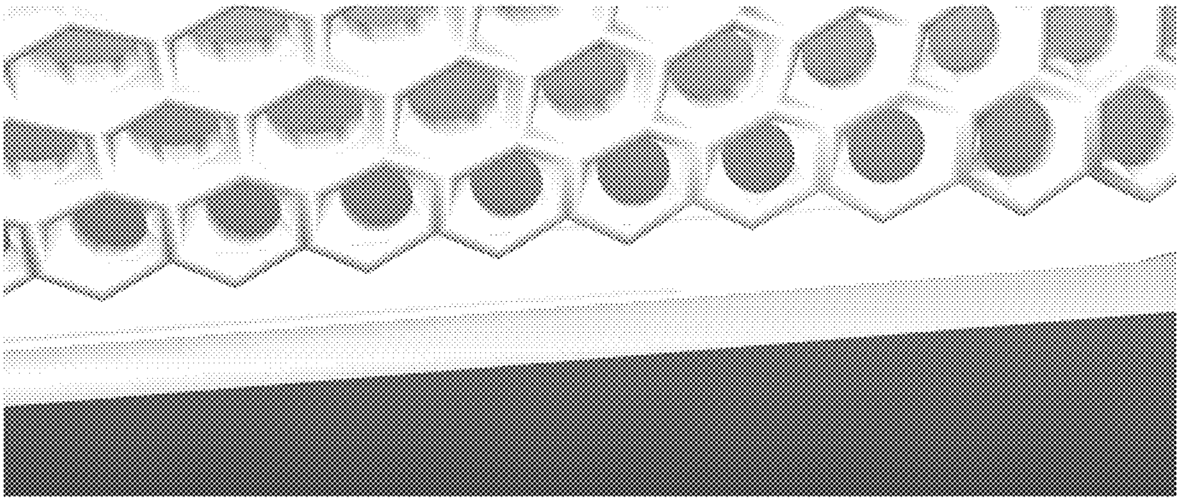
FIG. 14 shows a detailed view of a support portion of the fabricated immobilization device shown in FIG. 13 that extends from a patient immobilization region of the device to a baseplate connection frame and is configured to be absent from contact with the patient anatomy.
Figure 15:
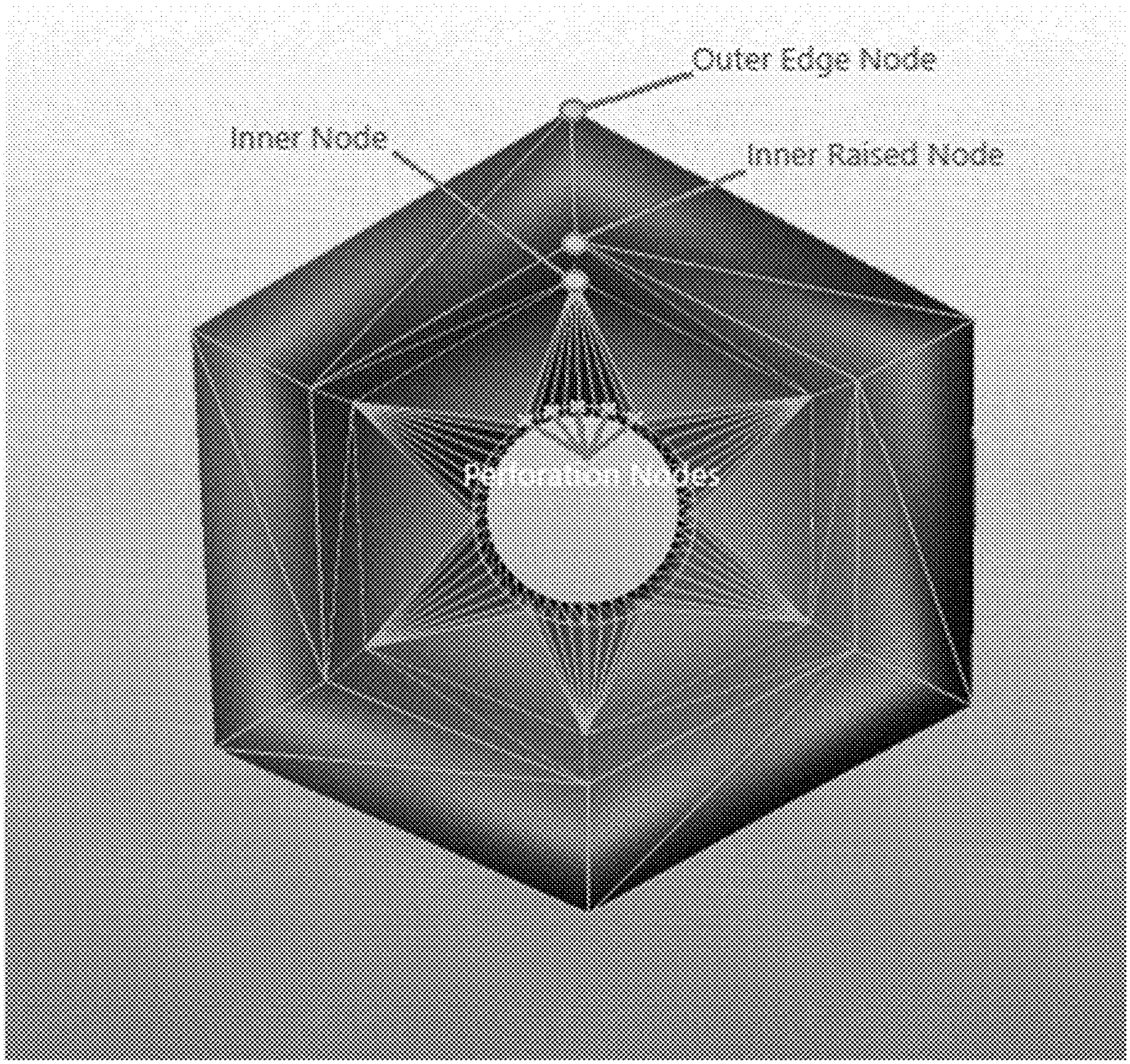
FIG. 15 shows an example design of a thin cellular region.

FIG. 13 shows an example fabricated immobilization device. FIG. 14 shows a detailed view of a support portion of the fabricated immobilization device shown in FIG. 13 that extends from a patient immobilization region of the device to a baseplate connection frame. The support portion is configured to be absent from contact with the patient anatomy when employed during clinical use. A solid infill region is employed to bridge the gap between the lowest row of cellular regions and the bottom frame of the immobilization device. FIG. 15 shows an example design of a thin cellular region.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

The invention claimed is:

1. An immobilization device for use in radiation therapy, said immobilization device comprising:
- a conformal shell layer having a first side shaped to conform to an anatomical region of a subject;
- a rigid lattice structure extending outwardly from a second side of said conformal shell layer, said rigid lattice structure dividing an exposed portion of the second side of said conformal shell layer into a plurality of thin cellular regions and conferring structural rigidity to said conformal shell layer; and
- a support portion extending from said conformal shell layer, said support portion comprising one or more fastening features positioned to secure the immobilization device to an immobilization baseplate of a radiation therapy system, such that when the immobilization device is secured to the immobilization baseplate via the one or more fastening features, the conformal shell layer contacts and immobilizes the anatomical region in a prescribed position and orientation.

2. The immobilization device according to claim 1 wherein said rigid lattice structure comprises a honeycomb lattice.

3. The immobilization device according to claim 1 wherein said conformal shell layer has a thickness between 0.4 mm and 1.0 mm.

4. The immobilization device according to claim 1 wherein said rigid lattice structure has a thickness between 0.4 mm and 1.0 mm.

5. The immobilization device according to claim 1 wherein said rigid lattice structure has a lateral width between 0.2 mm and 1.5 mm.

6. The immobilization device according to claim 1 wherein a radius of at least one cellular region of said plurality of cellular regions is between 2 mm and 8 mm.

7. The immobilization device according to claim 1 wherein one or more of said cellular regions are perforated.

8. The immobilization device according to claim 7 wherein one or more of said cellular regions is perforated with a perforation having a radius between 0.6 mm and 3 mm.

9. The immobilization device according to claim 1 wherein one or more geometrical parameters associated with said rigid lattice structure vary according to a local curvature of said conformal shell layer.

10. The immobilization device according to claim 1 wherein said conformal shell layer and said rigid lattice structure are formed from a thermoplastic.

11. The immobilization device according to claim 10 wherein the thermoplastic comprises PA12.

12. The immobilization device according to claim 10 wherein the thermoplastic comprises PLA.

13. The immobilization device according to claim 10 wherein the thermoplastic comprises PLA and hollow glass microspheres.

14. A method of fabricating an immobilization device for use in radiation therapy, the method comprising:
- obtaining surface data characterizing an anatomical region of a subject;
- employing the surface data to generate a digital model of an immobilization device according to claim 1; and
- employing a three-dimensional printer to fabricate the immobilization device according to the digital model.

15. The method according to claim 14 wherein the surface data is obtained using an optical surface scanning system.

16. The method according to claim 14 wherein the three-dimensional printer is a multi-jet fusion (MJF) three-dimensional printer.

17. The method according to claim 14 wherein the rigid lattice structure comprises a honeycomb lattice.

18. The method according to claim 14 wherein the conformal shell layer has a thickness between 0.4 mm and 1.0 mm.

19. The method according to claim 14 wherein the rigid lattice structure has a thickness between 0.4 mm and 1.0 mm.

20. The method according to claim 14 wherein the rigid lattice structure has a lateral width between 0.2 mm and 1.5 mm.

21. The method according to claim 14 wherein a radius of at least one cellular region of the plurality of cellular regions is between 2 mm and 8 mm.

22. The method according to claim 14 wherein one or more of the cellular regions are perforated.

23. The method according to claim 22 wherein one or more of the cellular regions is perforated with a perforation having a radius between 0.6 mm and 3 mm.

24. The method according to claim 14 wherein one or more geometrical parameters associated with the rigid lattice structure vary according to a local curvature of the conformal shell layer.

25. The method according to claim 14 wherein the conformal shell layer and the rigid lattice structure are formed from a thermoplastic.

26. The method according to claim 25 wherein the thermoplastic comprises PA12.

27. The method according to claim 25 wherein the thermoplastic comprises PLA.

28. The method according to claim 25 wherein the thermoplastic comprises PLA and hollow glass microspheres.

29. The immobilization device according to claim 1 wherein the support portion is configured to be absent of contact with the subject when the conformal shell is contacted with the anatomical region and the immobilization device is secured to the immobilization baseplate.

30. The immobilization device according to claim 1 wherein the support portion comprises a flange configured to contact the immobilization baseplate.

31. The immobilization device according to claim 1 wherein the flange comprises at least one fastening feature suitable for securing the immobilization device to the immobilization baseplate.

32. The immobilization device according to claim 1, wherein the rigid lattice structure and the conformal shell are integrally formed as a monolithic structure.

* * * * *